United States Patent [19]

Izydore et al.

[11] Patent Number: 5,192,761

[45] Date of Patent: * Mar. 9, 1993

[54] 1,2,4-TRIAZOLIDINE-3,5-DIONES AND 1,3,5-TRIAZINE-2,4(1-H,3H)-DIONES, PHARMACEUTICAL COMPOSITIONS

[75] Inventors: Robert A. Izydore, Durham; Iris H. Hall, Chapel Hill, both of N.C.

[73] Assignees: North Carolina Central Univ., Durham; University of North at Chapel Hill, Chapel Hill, both of N.C.

[*] Notice: The portion of the term of this patent subsequent to Sep. 12, 2006 has been disclaimed.

[21] Appl. No.: 609,750

[22] Filed: Nov. 6, 1990

Related U.S. Application Data

[62] Division of Ser. No. 224,680, Jul. 27, 1988, Pat. No. 5,034,528.

[51] Int. Cl.[5] .................. A61K 31/53; A61K 31/41
[52] U.S. Cl. ................................. 514/241; 514/384; 514/824
[58] Field of Search ............... 514/246, 384, 824, 241; 548/264; 544/223

[56] References Cited

U.S. PATENT DOCUMENTS

| | | | |
|---|---|---|---|
| 3,663,564 | 5/1972 | Jacobson et al. | 260/308 |
| 4,174,392 | 11/1979 | Möhring et al. | 514/241 |
| 4,433,085 | 2/1984 | Rottmaier et al. | 524/83 |
| 4,866,058 | 9/1989 | Izydore et al. | 514/241 |

Primary Examiner—Frederick E. Waddell
Assistant Examiner—Kimberly R. Jordan
Attorney, Agent, or Firm—Charles E. Smith

[57] ABSTRACT

The invention provides pharmaceutical compositions comprising hypolipidemically active derivatives of 1,2,4-triazolidine-3,5-diones, 1,3,5-triazabicyclo[3.1.0-]hexane-2,4-diones, and 1,3,5-triazine-2,4(1H,3H)-diones in a pharmaceutically acceptable carrier for treating hyperlipidemia in mammals, particularly humans.

5 Claims, No Drawings

1,2,4-TRIAZOLIDINE-3,5-DIONES AND 1,3,5-TRIAZINE-2,4(1-H,3H)-DIONES, PHARMACEUTICAL COMPOSITIONS

This is a division of application No. 07/224,680, now U.S. Pat. No. 5,034,528, filed Jul. 27, 1988.

FIELD OF THE INVENTION

The present invention relates to compositions having hypolipidemic activity and methods for their use in controlling hyperlipidemia in mammals. Specifically, the present invention is directed to methods for controlling hyperlipidemia by treating mammals, especially humans, with a class of hypolipidemic agents selected from 1,2,4-triazolidine-3,5-diones, 1,3,5-triazabicyclo[3.1.0]hexane-2,4-diones and 1,3,5-triazine-2,4(1$\underline{H}$,3$\underline{H}$)-diones.

BACKGROUND OF THE INVENTION

Cholesterol is commonly found in all the tissues and blood of mammals, especially humans. Manufactured in the liver and other cells as a substrate for other steroids and membrane synthesis; cholesterol is a normal constituent of bile. As will be appreciated, many familiar foods contain cholesterol, with some containing more than others. Maintaining proper levels of cholesterol in the body has become an important factor in todays diet, since medical science has proven that certain afflictions such as hypothyroidism, diabetes and the intake of foods having a high cholesterol content may result in high levels of cholesterol in the blood.

A condition which is associated with elevated levels of cholesterol, phospholipids, and/or triglycerides in the blood serum of mammals is common referred to as hyperlipidemia (i.e. as used herein, reference to hyperlipidemia is intended to be inclusive of both hypercholesterolemia and hypertriglyceremia, and hence, compounds having a hypolipidemic effect will exhibit activity to lower both cholesterol and triglyceride lipid levels). Hyperlipidemia can lead to serious health problems such as arthereosclerosis. We know that serum lipoprotein in mammals is composed of cholesterol together with triglyceride, phospholipid and apoproteins. Lipoprotein is composed of several fractions-the very low density lipoprotein (VLDL), the low density lipoprotein (LDL) and the high density lipoprotein (HDL) depending on the specific gravity of the aproprotein components of the fraction. Medical evidence points to the VLDL and LDL fractions as being associated with atherosclerosis. In contrast, the HDL fraction appears to carry cholesterol from the blood vessels to the liver where it is processed and excreted in the bile. As hyperlipidemic states increase in atherosclerosis the LDL cholesterol increases and HDL decreases. Effective hypolipidemic agents need to reverse this ratio since clinical data indicate that high HDL cholesterol and low LDL cholesterol protects man from myocardial infarctions. Thus, it is highly desirable to treat mammals afflicted with hyperlipidemia so as to lower VLDL and LDL fractions and increase the HDL fractions.

It is not surprising to find that a number of compounds have been proposed for the treatment of hyperlipidemia in mammals. Examples include U.S. Pat. No. 4,499,303 which describes the use of a novel class of N-benzoylsulfamates and benzoylsulfonamides as useful hypolipidemic agents. U.S. Pat. No. 4,395,417 proposes the use of cyclic imides, diones, reduced diones and analogs as useful agents. Crotic acid has been shown to decrease the plasma lipids blood level in rats.

U.S. Pat. No. 4,639,444 describes 3,5-dialkyl-4,6-diaryltetrahydro-2$\underline{H}$-1,3,5-thiadiazine-2-thione derivatives as useful hypolipidemic agents. U.S. Pat. No. 4,681,893 teaches that certain trans-6-[2-(3- or 4-carboxamido-substituted pyrrol-1-yl)alkyl]-4-hydroxypyran-2-ones and their ring opened acids are potent hypolipidemic agents. Likewise, U.S. Pat. No. 4,351,844 describes hypocholesterolaemic lactone compounds and their free acids which are derived from the natural fermentation product mevinolin. More recently, the control of hyperlipidemia through the use of a class of 4-pyrimidinecarboxylic acids has been described by Hall et al., *J. Pharm. Sci.* 74, 759 (1985).

In spite of the numerous compounds and methods which have been proposed for the control of hyperlipidemia, the need remains for drugs having enhanced lowering of elevated serum lipoprotein lipids.

Accordingly, it is the object of the present invention to provide a class of hypolipidemic compounds having enhanced capability in lowering LDL cholesterol and elevating HDL cholesterol. This and other objects of the present invention will be more apparent from the discussion which follows.

SUMMARY OF THE INVENTION

The present invention provides a method of controlling hyperlipidemia in mammals which comprises administering to a mammal an amount effective to control hyperlipidemia of a compound having hypolipidemic activity and the structural formula:

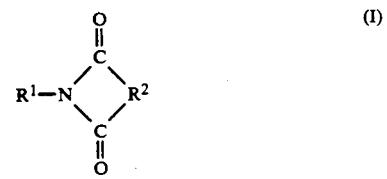

(I)

wherein $R^1$ is hydrogen, a $C_1$ to $C_{18}$ alkyl or substituted alkyl, a $C_2$ to $C_{18}$ alkenyl or substituted alkenyl, a $C_2$ to $C_{18}$ alkynyl or substituted alkynyl, a $C_4$ to $C_{10}$ cycloalkyl or substituted cycloalkyl, a $C_4$ to $C_{10}$ cycloalkenyl or substituted cycloalkenyl, phenyl, a substituted phenyl, phenalkyl, cyano, —CO—$R^9$ or —Y—CO—$R^9$; $R^2$ is

(a)

(b)

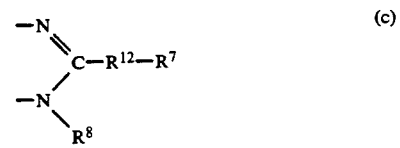

(c)

$R^3$ and $R^4$ can be the same or different and are each the same as $R^1$;

$R^5$, $R^6$ and $R^7$ can be the same or different and are each hydrogen, a $C_1$ to $C_{18}$ alkyl or substituted alkyl, a $C_2$ to $C_{18}$ alkenyl or substituted alkenyl, a $C_1$ to $C_{18}$ alkynyl or substituted alkynyl, a $C_4$ to $C_{10}$ cycloalkyl or substituted cycloalkyl, a $C_4$ to $C_{10}$ cycloalkenyl or substituted cycloalkenyl, phenyl or substituted phenyl, phenalkyl, $-CO-R^9$, or $-Y-CO-R^9$, with the proviso that $R^5$ and $R^6$ together cannot be so bulky as to cause the compound to decompose;

$R^8$ is hydrogen, a $C_1$ to $C_5$ alkyl, a $C_4$ to $C_{10}$ cycloalkyl, $-CO-R^9$, or $-Y-CO-R^9$;

$R^9$ is hydrogen, a $C_1$ to $C_5$ alkyl or substituted alkyl, a $C_2$ to $C_5$ alkenyl or substituted alkenyl, a $C_2$ to $C_5$ alkynyl or substituted alkynyl, phenyl or substituted phenyl, phenoxy or substituted phenoxy, a $C_1$ to $C_5$ alkoxy or substituted alkoxy, a $C_4$ to $C_{10}$ cycloalkyl or substituted cycloalkyl, a $C_4$ to $C_{10}$ cycloalkenyl or substituted cycloalkenyl, $-NHC_6C_5$, $-NR^{10}R^{11}$ wherein $R^{10}$ and $R^{11}$ can be the same or different and are each hydrogen, a $C_1$ to $C_5$ alkyl or substituted alkyl, phenyl or substituted phenyl;

$R^{12}$ is $-CO$, $-COH$, $-CS$, $-CSH$, or a $C_1$ to $C_4$ alkylene group; and Y is a $C_1$ to $C_{10}$ alkylene or substituted alkylene; and the pharmaceutically acceptable salts, and mixtures thereof.

In addition, the present invention provides for pharmaceutical compositions for use in controlling hyperlipidemia in mammals which comprises a hypolipidemically effective amount of a compound having hypolipidemic activity and a structural formula (I) or a pharmaceutically acceptable salt thereof as shown above in combination with a pharmaceutically acceptable carrier.

As referred to herein, "hypolipidemic activity" is intended to refer to the ability of the compounds of formula (I) to lower levels of serum cholesterol and/or triglycerides in mammals to which the compound is administered.

Many of the above-described compounds which may be used as hypolipidemic agents are new, and hence, as a further embodiment of the present invention there is provided a novel class of compounds having hypolipidemic activity and the structural formula:

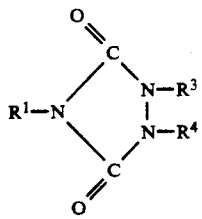

(II)

wherein $R^1$ is hydrogen, a $C_1$ to $C_{18}$ alkyl or substituted alkyl, a $C_2$ to $C_{18}$ alkenyl or substituted alkenyl, a $C_2$ to $C_{18}$ alkynyl or substituted alkynyl, a $C_4$ to $C_{10}$ cycloalkyl or substituted cycloalkyl, a $C_4$ to $C_{10}$ cycloalkenyl or substituted cycloalkenyl, phenyl, a substituted phenyl, phenalkyl, cyano, $-CO-R^9$ or $-Y-CO-R^9$;

$R^3$ and $R^4$ may be the same or different and are each the same as $R^1$;

$R^9$ is hydrogen, a $C_1$ to $C_5$ alkyl or substituted alkyl, a $C_2$ to $C_5$ alkenyl or substituted alkenyl, a $C_2$ to $C_5$ alkynyl or substituted alkynyl, phenyl or substituted phenyl, phenoxy or substituted phenoxy, a $C_1$ to $C_5$ alkoxy or substituted alkoxy, a $C_4$ to $C_{10}$ cycloalkyl or substituted cycloalkyl, a $C_4$ to $C_{10}$ cycloalkenyl or substituted cycloalkenyl, $-NHC_6C_5$, $-NR^{10}R^{11}$ wherein $R^{10}$ and $R^{11}$ can be the same or different and are each hydrogen, a $C_1$ to $C_5$ alkyl or substituted alkyl, phenyl or substituted phenyl; and Y is a $C_1$ to $C_{10}$ alkylene or substituted alkylene; provided that $R^3$ and $R^4$ are not both hydrogen and further provided that neither $R^3$ nor $R^4$ is hydrogen when $R^1$ is phenyl.

A second class of novel hypolipidemic agents according to this invention have the structural formula:

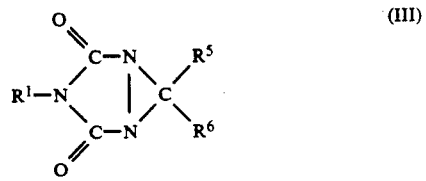

(III)

wherein $R^1$ is hydrogen, a $C_1$ to $C_{18}$ alkyl or substituted alkyl, a $C_2$ to $C_{18}$ alkenyl or substituted alkenyl, a $C_2$ to $C_{18}$ alkynyl or substituted alkynyl, a $C_4$ to $C_{10}$ cycloalkyl or substituted cycloalkyl, a $C_4$ to $C_{10}$ cycloalkenyl or substituted cycloalkenyl, phenyl, a substituted phenyl, cyano, phenalkyl, $-CO-R^9$ or $-Y-CO-R^9$;

$R^5$ and $R^6$ can be the same or different and are each hydrogen, a $C_1$ to $C_{18}$ alkyl or substituted alkyl, a $C_2$ to $C_{18}$ alkenyl or substituted alkenyl, a $C_2$ to $C_{18}$ alkynyl or substituted alkynyl, a $C_4$ to $C_{10}$ cycloalkyl or substituted cycloalkyl, a $C_4$ to $C_{10}$ cycloalkenyl or substituted cycloalkenyl, phenyl or substituted phenyl, phenalkyl, $-CO-R^9$, or $-Y-CO-R^9$, with the proviso that $R^5$ and $R^6$ together cannot be so bulky as to cause the compound to decompose;

$R^9$ is hydrogen, a $C_1$ to $C_5$ alkyl or substituted alkyl, a $C_2$ to $C_5$ alkenyl or substituted alkenyl, a $C_2$ to $C_5$ alkynyl or substituted alkynyl, phenyl or substituted phenyl, phenoxy or substituted phenoxy, a $C_1$ to $C_5$ alkoxy or substituted alkoxy, a $C_4$ to $C_{10}$ cycloalkyl or substituted cycloalkyl, a $C_4$ to $C_{10}$ cycloalkenyl or substituted cycloalkenyl, $-NHC_6C_5$, $-NR^{10}R^{11}$ wherein $R^{10}$ and $R^{11}$ can be the same or different and are each hydrogen, a $C_1$ to $C_5$ alkyl or substituted alkyl, phenyl or substituted phenyl; and Y is a $C_1$ to $C_{10}$ alkylene or substituted alkylene; and the pharmaceutically acceptable salts thereof, and mixtures thereof;

provided that $R^1$ is not phenyl or chlorophenyl when $R^5$ is hydrogen, $R^6$ is $-CO-R^9$, and $R^9$ is ethoxy or when $R^6$ is hydrogen, $R^5$ is $-CO-R^9$, and $R^9$ is ethoxy; and further provided that $R^1$ is not phenyl when $R^5$ is hydrogen, $R^6$ is $-CO-R^9$, and $R^9$ is methoxy or when $R^6$ is hydrogen, $R^5$ is $-CO-R^9$, and $R^9$ is methoxy.

A third class of novel hypolipidemic agents according to this invention have the structural formula:

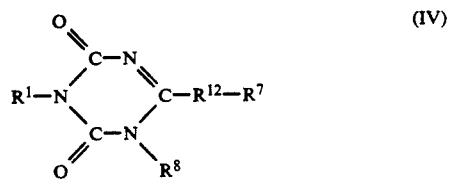

(IV)

wherein $R^1$ is hydrogen, a $C_1$ to $C_{18}$ alkyl or substituted alkyl, a $C_2$ to $C_{18}$ alkenyl or substituted alkenyl, a $C_2$ to $C_{18}$ alkynyl or substituted alkynyl, a $C_4$ to $C_{10}$ cycloalkyl or substituted cycloalkyl, a $C_4$ to $C_{10}$ cycloalkenyl or substituted cycloalkenyl, phenyl, a substituted phenyl, cyano, phenalkyl, —CO—$R^9$ or —Y—CO—$R^9$;

$R^7$ is hydrogen, a $C_1$ to $C_{18}$ alkyl or substituted alkyl, a $C_2$ to $C_{18}$ alkenyl or substituted alkenyl, a $C_2$ to $C_{18}$ alkynyl or substituted alkynyl, a $C_4$ to $C_{10}$ cycloalkyl or substituted cycloalkyl, a $C_4$ to $C_{10}$ cycloalkenyl or substituted cycloalkenyl, phenyl or substituted phenyl, phenalkyl, —CO—$R^9$, or —Y—CO—$R^9$, $R^8$ is hydrogen, a $C_1$ to $C_5$ alkyl, a $C_4$ to $C_{10}$ cycloalkyl, —CO—$R^9$, or —Y—CO—$R^9$;

$R^9$ is hydrogen, a $C_1$ to $C_5$ alkyl or substituted alkyl, a $C_2$ to $C_5$ alkenyl or substituted alkenyl, a $C_2$ to $C_5$ alkynyl or substituted alkynyl, phenyl or substituted phenyl, phenoxy or substituted phenoxy, a $C_1$ to $C_5$ alkoxy or substituted alkoxy, a $C_4$ to $C_{10}$ cycloalkyl or substituted cycloalkyl, a $C_4$ to $C_{10}$ cycloalkenyl or substituted cycloalkenyl, —NHC$_6$C$_5$, —NR$^{10}$R$^{11}$ wherein $R^{10}$ and $R^{11}$ can be the same or different and are each hydrogen, a $C_1$ to $C_5$ alkyl or substituted alkyl, phenyl or substituted phenyl;

$R^{12}$ is —CO, —COH, —CS, —CSH, or a $C_1$ to $C_4$ alkylene group; and

Y is a $C_1$ to $C_{10}$ alkylene or substituted alkylene;

with the proviso that when $R^8$ is hydrogen and $R^7$ is ethoxy, $R^1$ is not phenyl, chlorophenyl, methoxyphenyl, or n-butyl.

Pharmaceutically acceptable salts and mixtures of the above-described compounds are expected to have similar activity.

DETAILED DESCRIPTION OF THE INVENTION

We have found that the above-described compounds of formulas (I) through (IV) effectively lower serum lipids in mammals. The term mammals as used herein is intended in its normal sense, and hence is inclusive of not only mice, rats, dogs, cats, horses, pigs, sheeps, cows and other animals, but humans as well. Through the use of the hypolipidemic agents of the present invention, we observed the inhibition of activity of the rate limiting enzyme of cholesterol synthesis (HMG CoA reductase) as well as the lowering of the acyl CoA cholesterol acyl transferase (cholesterol ester), acetyl CoA carboxylase (fatty acid), sn glycerol-3-phosphate acyl transferase and phosphatidylate phosphohydrolase (triglyceride) and heparin induced lipoprotein lipase (release of triglycerides for apoproteins).

The hypolipidemic agents of the present invention afford reduction in both serum cholesterol and triglycerides and can be used in lower dosage amounts than commercially available agents such as nicotinic acid derivatives, clofibrate, cholestyramine and cholesripol. Through the use of the agents of the present invention we have observed significant increases in HDL-cholesterol and reduced levels of LDL cholesterol with an acceleration of lipid excretion via the feces with clearance of lipids from the blood compartment and tissues, e.g. the aorta wall.

As used herein, the terms "alkyl", "alkenyl", "cycloalkenyl", "cycloalkyl" and "alkoxy" refer to carbon containing substituents that may be straight chain or branched. The terms "substituted alkyl", "substituted alkenyl", "substituted alkynyl", "substituted cycloalkyl", "substituted cycloalkenyl" and "substituted alkoxy" include those substituted with at least one common functional substituent selected from but not limited to the group consisting of alkoxy, oxo, alkoxy carbonyl, halogen, nitro, aryl, carbamoyl, amino, amido, acyloxy, hydroxy, carboxy, alkylthio, sulfoxide, sulfone, thiol, sulfonyl, sulfano, phosphono and silyl. Thus, examples of alkyl groups include methyl, ethyl, n-propyl, isopropyl, n-butyl, and n-pentyl, Examples of alkoxy groups include methoxy and ethoxy. Exemplary of suitable cycloalkyl groups are cyclobutyl, cyclopentyl or cyclohexyl.

The terms "substituted phenyl" and "substituted phenoxy" refer to the presence on the aromatic ring of at least one common functional substituent selected from but not limited to the group of $C_1$ to $C_5$ alkyl, substituted $C_1$ to $C_5$ alkyl, $C_1$ to $C_5$ alkoxy, benzoyl, alkanoyl, alkoxy carbonyl, halogen, nitro, carbamoyl, amino, amido, acyloxy, hydroxy, carboxy, alkylthio, sulfoxide, sulfone, thiol, sulfonyl, sulfano, phosphono and silyl.

Halogen groups may be selected from bromine, chlorine, fluorine and iodine, and preferably from chlorine and bromine.

Our invention provides a method for treating hypolipidemia in mammals by administering a hypolipidemically effective amount of a compound of formula (I). Examples of compounds of formula (I) wherein $R^2$ is (A) are those wherein $R^1$ is selected from the group consisting of phenyl, halophenyl, alkylphenyl wherein the alkyl group has from 1 to 5 carbon atoms, alkoxyphenyl wherein the alkoxy group has from 1 to 5 carbon atoms, nitrophenyl, and alkyl having from 1 to 5 carbon atoms; and $R^3$ and $R^4$ may be the same or different and are each selected from the group consisting of hydrogen, alkylcarbonyl wherein the alkyl group has from 1 to 5 carbon atoms, alkoxycarbonyl wherein the alkoxy group has from 1 to 5 carbon atoms, and N-phenylcarbamoyl. Specific compounds of formula (I) wherein $R^2$ is (a) include 4-phenyl-1-methylcarbonyl-1,2,4-triazolidine-3,5-dione, 4-phenyl-1,2-dimethylcarbonyl-1,2,4-triazolidine-3,5-dione, 4-phenyl-1-N-phenylcarbamoyl-1,2,4-triazolidine-3,5-dione, 4-phenyl-1-ethoxycarbonyl-1,2,4-triazolidine-3,5-dione, 4-(4-chlorophenyl)-1-methylcarbonyl-1,2,4-triazolidine-3,5-dione, 4-(4-methoxyphenyl)-1,2,4-triazolidine-3,5-dione, 4-n-butyl-1,2,4-triazolidine-3,5-dione, 4-(4-nitrophenyl)-1,2,4-triazolidine-3,5-dione, 4-(4-chlorophenyl)-1,2,4-triazolidine-3,5-dione, 4-methyl-1,2,4-triazolidine-3,5-dione, 4-phenyl-1,2,4-triazolidine-3,5-dione, 4-(4-methoxyphenyl)-1,2-dimethylcarbonyl-1,2,4-triazolidine-3,5-dione, 4-(4-methoxyphenyl-1,2-di-n-pentylcarbonyl-1,2,4-triazolidine-3,5-dione, 4-(4-methoxyphenyl)1,2-diethylcarbonyl-1,2,4-triazolidine-3,5-dione, 4-(4-nitrophenyl)-1,2-diethylcarbonyl-1,2,4-triazolidine-3,5-dione, 4-n-butyl-1,2-di-n-pentylcarbonyl-1,2,4-triazolidine-3,5-dione, 4-(4-chlorophenyl)-1,2-dimethylcarbonyl-1,2,4-triazolidine-3,5-dione, 4-(4-chlorophenyl)-1-methylcarbonyl-1,2,4-triazolidine-3,5-dione, 4-(4-chlorophenyl)-1-phenylcarbonyl-1,2,4-triazolidine-3,5-dione, 4-(4-chlorophenyl)-1-n-propylcarbonyl-1,2,4-triazolidine-3,5-dione, 4-(4-chlorophenyl)-1-n-pentylcarbonyl-1,2,4-triazolidine-3,5-dione, 4-(4-chlorophenyl)-1-n-butylcarbonyl-1,2,4-triazolidine-3,5-dione, 4-(4-chlorophenyl)1-ethylcarbonyl-1,2,4-triazolidine-3,5dione, 4-(4-methoxyphenyl)-1-methylcarbonyl-1,2,4-triazolidine-3,5-dione, 4-(4-methoxyphenyl)-1-benzoyl-1,2,4-triazolidine-3,5-dione, 4-(4-methoxyphenyl)-1-n-propylcarbonyl-1,2,4-triazolidine-3,5-dione, 4-(4-methoxyphenyl)-1-n-pentylcarbonyl-1,2,4-triazolidine-3,5-dione, 4-(4-methoxyphenyl)-1-n-butylcarbonyl-1,2,4-triazolidine-3,5-dione, 4-(4-methoxyphenyl)-1-ethylcarbonyl-1,2,4-triazolidine-3,5-dione, 4-(4-methoxyphenyl)-1-trichloromethylcarbonyl-1,2,4-triazolidine-3,5-dione, 4-(4-nitrophenyl)-1-methylcarbonyl-1,2,4-triazolidine-3,5-dione, 4-(4-nitrophenyl)-1-benzoyl-1,2,4-triazolidine-3,5-dione, 4-(4-nitrophenyl)-1-n-propylcarbonyl-1,2,4-triazolidine-3,5-dione, 4-(4-nitrophenyl)-1-n-pentylcarbonyl-1,2,4-triazolidine-3,5-dione, 4-(4-nitrophenyl)-1-n-butylcarbonyl-1,2,4-triazolidine-3,5-dione, 4-(4-nitrophenyl)-1-ethylcarbonyl-1,2,4-triazolidine-3,5-dione, 4-(4-nitrophenyl)-1-trichloromethylcarbonyl-1,2,4-trizolidine-3,5-dione, 4-n-butyl-1-benzoyl-1,2,4-triazolidine-3,5-dione, 4-n-butyl-1-methylcarbonyl-1,2,4-triazolidine-3,5-dione, 4-n-butyl-1-n-propylcarbonyl-1,2,4-triazolidine-3,5dione, 4-n-butyl-1-n-pentylcarbonyl-1,2,4-triazolidine-3,5-dione, 4-n-butyl-1-n-butylcarbonyl-1,2,4-triazolidine-3,5-dione, and 4-n-butyl-1-ethylcarbonyl-1,2,4-triazolidine-3,5-dione, and 4-n-butyl-1-trichloromethylcarbonyl-1,2,4-triazolidine-3,5-dione, 4phenyl-1-(3,4,5-trimethoxybenzoyl)-1,2,4-triazolidine-3,5dione, 4-(4-chlorophenyl)-1-(3,4,5-trimethoxybenzoyl)-1,2,4-triazolidine-3,5-dione, 4-(4-methoxyphenyl)-1-(3,4,5-trimethoxybenzoyl)-1,2,4-triazolidine-3,5-dione, 4-(4-nitrophenyl)-1-(3,4,5-trimethoxybenzoyl)-1,2,4-triazolidine-3,5-dione, 4-n-butyl-1-(3,4,5-trimethoxybenzoyl)-1,2,4-triazolidine-3,5-dione, 4-phenyl-1,2-bis-(3,4,5-trimethoxybenzoyl)-1,2,4-triazolidine-3,5-dione, 4-(4-chlorophenyl-1,2-bis-(3,4,5-trimethoxybenzoyl)-1,2,4-triazolidine-3,5-dione, 4-(4-methoxyphenyl)-1,2-bis-(3,4,5-trimethoxybenzoyl)-1,2,4-triazolidine-3,5-dione, 4-(4-nitrophenyl)-1,2-bis-(3,4,5-trimethoxybenzoyl)-1,2,4-triazolidine-3,5-dione, 4-n-butyl-1,2-bis-(3,4,5-trimethoxybenzoyl)-1,2,4-triazolidine-3,5-dione, and pharmaceutically acceptable salts and mixtures thereof.

Compounds of formula (I) wherein $R^2$ is (b) include those wherein $R^1$ is selected from the group consisting of phenyl, halophenyl, alkylphenyl wherein the alkyl group has from 1 to 5 carbon atoms, alkoxyphenyl wherein the alkoxy group has from 1 to 5 carbon atoms, nitrophenyl, and alkyl having from 1 to 5 carbon atoms; and $R^5$ and $R^6$ are the same or different and are each selected from the group consisting of hydrogen, alkoxycarbonyl wherein the alkoxy group has from 1 to 5 carbon atoms, alkylcarbonyl wherein the alkyl group has from 1 to 5 carbon atoms, phenoxycarbonyl, carbamoyl and substituted carbamoyl. It is appreciated that, if $R^5$ and $R^6$ are too bulky, such as in the case when both are aromatic, the compound wherein $R^2$ is (b) may decompose. Thus those compounds are intended to be excluded from the invention.

Exemplary of compounds of formula (I) wherein $R^2$ is (b) are 3-(4-chlorophenyl)-6-ethoxycarbonyl-1,3,5-triazabicyclo[3.1.0]hexane-2,4dione, 3-phenyl-6-ethoxycarbonyl-1,3,5-triazabicyclo[3.1.0]hexane-2,4-dione, 3-(4-methoxyphenyl)-6-ethoxycarbonyl-1,3,5-triazabicyclo[3.1.0]hexane-2,4-dione, 4-n-butyl-6-ethoxycarbonyl-1,3,5-triazabicyclo[3.1.0]hexane-2,4-dione, 3-phenyl-6-methoxycarbonyl-1,3,5-triazabicyclo[3.1.0]hexane-2,4-dione and pharmaceutically acceptable salts and mixtures thereof.

Compounds of formula (I) wherein $R^2$ is (c) include those wherein $R^1$ is selected from the group consisting of phenyl, halophenyl, alkylphenyl wherein the alkyl group has from 1 to 5 carbon atoms, alkoxyphenyl wherein the alkoxy group has from 1 to 5 carbon atoms, nitrophenyl, and alkyl having from 1 to 5 carbon atoms; $R^7$ is an alkoxy having from 1 to 5 carbon atoms or phenoxy; and $R^8$ is hydrogen or a $C_1$ to $C_5$ alkyl; and $R^{12}$ is —CO. Exemplary of the compounds of formula (I) wherein $R^2$ is (c) are 3-phenyl-6-ethoxycarbonyl-1,3,5-triazine-2,4(1H,3H)-dione; 3-(4-chlorophenyl)-6-ethoxycarbonyl-1,3,5-triazine-2,4(1H,3H)-dione; and pharmaceutically acceptable salts and mixtures thereof.

According to a further aspect, our invention provides novel compounds of formula (II) as defined above with the proviso that provided that both $R^3$ and $R^4$ are not hydrogen and that $R^1$ is not phenyl when either $R^3$ and $R^4$ is hydrogen and further provided that $R^9$ is not —NHC$_6$H$_5$ when $R^1$ is phenyl. Our invention further provides novel compounds of formula (III) as defined above provided that $R^1$ is not phenyl or chlorophenyl when $R^5$ is hydrogen, $R^6$ is —CO—$R^9$, and $R^9$ is ethoxy or when $R^6$ is hydrogen, $R^5$ is —CO—$R^9$, and $R^9$ is ethoxy; and further provided that $R^1$ is not phenyl when $R^5$ is hydrogen, $R^6$ is —CO—$R^9$, and $R^9$ is methoxy or when $R^6$ is hydrogen, $R^5$ is —CO—$R^9$, and $R^9$ is methoxy. Novel compounds of formula (IV) as defined above are also provided with the proviso that when $R^8$ is hydrogen and $R^7$ is ethoxy, $R^1$ is not phenyl, chlorophenyl, methoxyphenyl, or n-butyl.

Included compounds from within the class defined by formula (II) are those wherein $R^1$ is selected from the group consisting of halophenyl, alkylphenyl wherein the alkyl group has from 1 to 5 carbon atoms, alkoxyphenyl wherein the alkoxy group has from 1 to 5 carbon atoms, and nitrophenyl; and $R^3$ and $R^4$ are each selected from the group consisting of hydrogen, alkylcarbonyl wherein the alkyl group has from 1 to 5 carbon atoms, alkoxycarbonyl wherein the alkoxy group has from 1 to 5 carbon atoms, and a carbamoyl or substituted carbamoyl with the proviso that both $R^3$ and $R^4$ are not both hydrogen.

Exemplary of novel hypolipidemic compounds of formula (II) are 4-phenyl-1-methylcarbonyl-1,2,4-triazolidine-3,5dione, 4-phenyl-1,2-dimethylcarbonyl-1,2,4-triazolidine-3,5-dione, 4-(4-chlorophenyl-1-methylcarbonyl-1,2,4-triazolidine-3,5-dione, 4-(4-methoxyphenyl)-1,2-dimethylcarbonyl-1,2,4-triazolidine-3,5-dione, 4-(4-methoxyphenyl-1,2-di-n-pentylcarbonyl-1,2,4-triazolidine-3,5-dione, 4-(4-methoxyphenyl)-1,2-diethylcarbonyl-1,2,4-triazolidine-3,5-dione, 4-(4-nitrophenyl)-1,2-diethylcarbonyl-1,2,4-triazolidine-3,5-dione, 4-n-butyl-1,2-di-n-pentylcarbonyl-1,2,4-triazolidine-3,5-dione, 4-(4-chlorophenyl)-1,2-dimethylcarbonyl-1,2,4-triazolidine-3,5-dione, 4-(4-chlorophenyl)-1-methylcarbonyl-1,2,4-triazolidine-3,5-dione, 4-(4-chlorophenyl)-1-benzoyl-1,2,4-triazolidine-3,5dione, 4-(4-chlorophenyl)-1-n-pentylcarbonyl-1,2,4-triazolidine-3,5-dione, 4-(4-chlorophenyl)1-n-butylcarbonyl-1,2,4-triazolidine-3,5-dione, 4-(4-methoxyphenyl)-1-methylcarbonyl-1,2,4-triazolidine-3,5-dione, 4-(4-methoxyphenyl)-1-benzoyl-1,2,4-triazolidine-3,5-dione, 4-(4-methoxyphenyl)-1-n-propylcarbonyl-1,2,4-triazolidine-3,5-dione, 4-(4-methoxyphenyl)-1-n-pentylcarbonyl-1,2,4-triazolindine-3,5-dione, 4-(4-methoxyphenyl)-1-n-butylcarbonyl-1,2,4-triazolidine-3,5-dione, 4-(4-methoxyphenyl)-1-trichloromethylcarbonyl-1,2,4-triazolidine-3,5-dione, 4-(4-nitrophenyl)-1-methylcarbonyl-1,2,4-triazolidine-3,5-dione, 4-(4-nitrophenyl)-1-benzoyl-1,2,4-triazolidine-3,5-dione, 4-(4-nitrophenyl)-1-n-propylcarbonyl-1,2,4-triazolidine-3,5-dione, 4-(4-nitrophenyl)-1-n-pentylcarbonyl-1,2,4-triazolidine-3,5- dione, 4-(4-nitrophenyl)-1-n-butylcarbonyl-1,2,4-triazolidine-3,5-dione, 4-(4-nitrophenyl)-1-ethylcarbonyl-1,2,4-triazolidine-3,5-dione, 4-(4-nitrophenyl)-1-trichloromethylcarbonyl-1,2,4-triazolidine-3,5-dione, 4-n-butyl-1-benzoyl-1,2,4-triazolidine-3,5-dione, 4-n-butyl-1-methylcarbonyl-1,2,4-triazolidine-3,5-dione, 4-n-butyl-1-n-propylcarbonyl-1,2,4-triazolidine-3,5-dione, 4-n-butyl-1-n-pentylcarbonyl-1,2,4-triazolidine-3,5-dione, 4-n-butyl-1-n-butylcarbonyl-1,2,4-triazolidine-3,5-dione, and 4-n-butyl-1-trichloromethylcarbonyl-1,2,4-triazolidine-3,5-dione, 4-phenyl-1-(3,4,5-trimethoxybenzoyl)-1,2,4-triazolidine-3,5-dione 4-(4-chlorophenyl)-1-(3,4,5-trimethoxybenzoyl)-1,2,4-triazolidine-3,5-dione, 4-(4-methoxyphenyl)-1-(3,4,5-trimethoxybenzoyl)-1,2,4-triazolidine-3,5-dione, 4-(4-nitrophenyl)-1-(3,4,5-trimethoxybenzoyl)-1,2,4-triazolidine-3,5-dione, 4-n butyl-1-(3,4,5-trimethoxybenzoyl)-1,2,4-triazolidine-3,5-dione, 4-phenyl-1,2-bis-(3,4,5-trimethoxybenzoyl)-1,2,4-triazolidine-3,5-dione, 4-(4-chlorophenyl)-1,2-bis-(3,4,5-trimethoxybenzoyl)-1,2,4-triazolidine-3,5-dione, 4-(4-methoxyphenyl)-1,2-bis-(3,4,5-trimethoxybenzoyl)-1,2,4-triazolidine-3,5-dione, 4-(4-nitrophenyl)-1,2-bis-(3,4,5-trimethoxybenzoyl)-1,2,4-triazolidine-3,5-dione, 4-n-butyl-1,2-bis-(3,4,5-trimethoxybenzoyl)-1,2,4-triazolidine-3,5-dione, and pharmaceutically acceptable salts and mixtures thereof.

Novel compounds from within the class defined by formula (III) include those wherein $R^1$ is selected from the group consisting of phenyl, halophenyl, alkylphenyl wherein the alkyl group has from 1 to 5 carbon atoms, alkoxyphenyl wherein the alkoxy group has from 1 to 5 carbon atoms, nitrophenyl, and alkyl having from 1 to 5 carbon atoms; and $R^5$ and $R^6$ may be the same or different and are each selected from the group consisting of hydrogen and alkoxycarbonyl wherein the alkoxy group has from 1 to 5 carbon atoms.

Exemplary of novel hypolipidemic compounds of formula (III) are 3-(4-methoxyphenyl)-6-ethoxycarbonyl-1,3,5-triazabicyclo[3.1.0]hexane-2,4-dione, 3-n-butyl-6-ethoxycarbonyl-1,3,5-triazabicyclo[3.1.0]hexane-2,4-dione, 3-(4-nitrophenyl)-6-ethoxycarbonyl-1,3,5-triazabicyclo[3.1.0]hexane-2,4-dione and pharmaceutically acceptable salts and mixtures thereof.

Compounds from within the class defined by formula (IV) include those where $R^1$ is selected from the group consisting of halophenyl, nitrophenyl and alkoxyphenyl wherein the alkoxy group contains from 1 to 5 carbon atoms but is not ethoxy when $R^1$ is chlorophenyl.

As noted, the pharmaceutically acceptable salts of the compounds of formulas (I) through (IV) can be used. These salts may be acid addition salts formed from inorganic or organic, e.g. hydrochlorides, sulfates, phosphates, benzoates or acetates, or salts formed with bases, e.g. alkali metal salts such as sodium or potassium salts.

The amount of hypolipidemically active compound as defined by formulas (I) through (IV) (including esters and pharmaceutically acceptable salts thereof) which is required for the treatment of patients suffering from elevated lipid levels will vary with the route of administration, the condition of the patient under treatment and is ultimately at the discretion of the attending physician. However, a suitable dose of the active compound is the range of from about 1 to about 100 mg/kg body weight per day; preferably from about 4 to about 16 mg/kg daily. Thus, for example, when administered to man (of approximately 70 kg body weight) in multiple daily doses, a typical unit or sub-dose of the active compound is about 150 mg.

The form of the dose is not critical and may be formulated for oral, buccal, parenteral or rectal administration or in a form suitable for administration by inhalation or inefflation. Oral administration is preferred.

Tablets and capsules for oral administration may contain conventional excipients such as binding agents, for example mucilage of starch or polyvinylpyrrolidone; fillers, for example, lactose, microcrystalline cellulose or maize-starch; lubricants, for example, magnesium stearate or stearic acid; disintegrants, for example, potato starch, croacarmellose sodium or sodium starch glycollate; or wetting agents such as sodium lauryl sulphate. The tablets may be coated according to methods well known in the art.

Oral liquid preparations may be in the form of, for example, aqueous or oily suspensions, solutions, emulsions, syrups or elixirs, or may be presented as a dry product for constitution with water or another suitable vehicle before use. Such liquid preparations may contain conventional additives such as suspending agents, for example, sorbitol syrup, methyl cellulose, glucose/sugar syrup or carboxymethyl cellulose; emulsifying agents, for example, sorbitan mono-oleate; non-aqueous vehicles (which may include edible oils), for example, propylene glycol or ethyl alcohol; and preservatives, for example, methyl or propyl p-hydroxybenzoates or sorbic acid. Suitably, a 1% aqueous solution of carboxymethylcellulose may be employed.

The compounds of formulas (I) through (IV) or their salts may also be formulated as suppositories, e.g. containing conventional suppository bases such as cocoa butter or other glycerides.

For buccal administration, the composition may take the form of tablets or lozenges formulated in conventional manner.

The compounds of formulas (I) through (IV) and their physiologically acceptable acid addition or basic salts may be formulated for parenteral administration by injection or continuous infusion and may be presented in unit dose form in ampoules, or in multi-dose forms with an added preservative.

The compositions may take such forms as suspensions, solutions, or emulsions in oily or aqueous vehicles, and may contain formulatory agents such as suspending, stabilizing, and/or dispersing agents. Alternatively, the active ingredient may be in power form for constitution with a suitable vehicle, e.g. sterile, pyrogen-free water, before use.

It will therefore be appreciated that the compounds of formulas (I) through (IV) or their pharmaceutically acceptable salts, may be used in the manufacture of a medicament for the treatment of human or animal subjects suffering from hyperlipidemia.

EXPERIMENTAL

Melting points and boiling points are uncorrected. Infrared spectra were recorded on a Beckman Acculab 10 spectrophotometer. Ultraviolet spectra were obtained on a Beckman DBG spectrophotometer. $^1H$ NMR spectra were recorded on a Varian EM-360A spectrometer. Mass spectra were determined on an AEI-902 mass spectrometer at the Research Triangle Institute of Mass Spectrometry, Research Triangle Park, N.C. Elemental analyses were performed by Integral Microanalytical Laboratories, Raleigh, N.C. and Desert Analytics, Phoenix, Ariz.

Generally, derivatives of 1,2,4-triazolidine-3,5-diones (Compounds of formula (I)(a) and (II)) may be synthesized by reacting 4-substituted 1,2,4-triazolidine-3,5-diones synthesized by the stepwise procedure of Cookson, Gupte, Stevens, and Watts, Org. Syn. 1871, 51, 121, with carboxylic acid anhydrides or alkoxy chloroformates wherein the alkoxy group has from 1 to 5 carbon atoms in the presence of sodium hydride, or aryl isocyanates in the presence of sodium hydride. 1- and 1,2-alkyl substituted derivatives can be made by reacting 4-substituted 1,2,4-triazolidine-3,5-diones with alkyl halides or cycloalkyl halides in the presence of a base, e.g. KOH. This latter method can also be used to prepare alkenyl, cycloalkenyl and alkynyl derivatives so long as the multiply bonded group is not directly attached to the ring nitrogen. To attach a phenyl in the $R^3$ or $R^4$ position, phenylhydrazine should be used to cyclize the triazolidine-3,5-dione ring.

Derivatives of 1,3,5-triazine-2,4-(1H,3H)-diones (Compounds of formula (I)(c) and (IV) may be synthesized by heating a solution of a compound of formula (I)(b) or (III) in chlorobenzene at reflux at 2 weeks.

The following specific examples illustrate the preparation of compounds defined by formulas (I) through (IV) and are according to the invention, but are not to be construed as limiting the scope thereof.

Preparation of Compounds of Formula (I)(a) and (II)

The 4-substituted 1,2,4-triazolidine-3,5-diones were prepared by the stepwise procedure of Cookson, Gupte, Stevens and Watts, Org. Synth. 1971, 51, 121.

General Procedure for the Synthesis of the 1-Alkylcarbonyl-4-substituted-1,2,4-triazolidine-3,5diones: To a stirred suspension of the 4-substituted 1,2,4-triazolidine-3,5-dione (30 mmol) in 150 to 200 ml of chloroform at room temperature was added dropwise the carboxylic acid anhydride or other appropriate aclyating agent (450 mmol). The reaction mixture was stirred at room temperature or heated under reflux, as required, for one to five days. The reaction mixture was filtered to remove the 1-acylated 4-substituted 1,2,4-triazolidine-3,5-dione and unreacted 1,2,4-triazolidine-3,5-dione. This solid mixture was not always present depending on the anhydride used in the reaction. Treatment of the filtered solid with water removed the unreacted 1,2,4-triazolidine-3,5-dione to give the 1-alkylcarbonyl-1,2,4-triazolidine-3,5-dione, which was purified by recrystallization from ethanol:water. The filtrate was washed with three 100 ml portions of water and three 80 ml portions of 10% sodium carbonate. The carbonate washings were acidified with concentrated hydrochloric acid to precipitate an additional quantity of the 1-alkylcarbonyl-4-substituted-1,2,4-triazolidine-3,5-dione.

Preparation of 1-Methylcarbonyl-4-phenyl-1,2,4-triazolidine-3,5-dione: To a suspension of 5.3 g (30 mmol) of 4-phenyl-1,2,4-triazolidine-3,5-dione in 175 ml of chloroform was added dropwise over a 15 minute period 45.9 g (450 mmol) of acetic anhydride with stirring. The reaction mixture was stirred at room temperature for five days. The reaction mixture was filtered to remove a white precipitate which was washed with 30 ml of chloroform to give 3.55 g (54.0%) of 1-methylcarbonyl-4-phenyl-1,2,4-triazolidine-3,5-dione as white solid, m.p. 215°–218.5° C. The filtrate was washed with three 100 ml portions of water and three 80 portions of 10% sodium carbonate. The carbonate washings were acidified with concentrated hydrochloric acid. No precipitate was formed. The chloroform solution was dried ($Na_2SO_4$) and evaporated under reduced pressure to give a liquid residue containing acetic anhydride. The filtered solid was recrystallized from 95% to ethanol to yield pure 1-methylcarbonyl-4-phenyl-1,2,4-triazolidine-3,5-dione; m.p. 216.5°–218.5° C.; IR (Nujol) 1726, 1710, 1688 cm$^{-1}$ (CO); $^1$H NMR (60 MHz, $CDCl_3$)δ7.90 (s, 5H) 2.55(s, 3H). Found C, 54.5; H, 4.2: N, 19.4. $C_{10}H_9N_3O_3$ requires C, 54.8; H, 4.2; N, 19.4

Preparation of 1-Methylcabonyl-4-(4-chlorophenyl)-1,2,4-triazolidine-3,5-dione: To a suspension of 6.38 g (30 mmol) of 4-(4-chlorophenyl-1,2,4-triazolidine-3,5-dione in 175 ml of chloroform was added dropwise over a 15 minute period 45.9 g (450 mmol) of acetic anhydride with stirring. The reaction mixture was stirred at room temperature for five days. The reaction mixture was filtered. The filtrate was washed with three 100 ml portions of water and three 80 ml portions of 10% sodium carbonate. The carbonate washings were acidified with concentrated hydrochloric acid to yield a precipitate of the triazolidine-3,5-dione product. In some instances a precipitate, which was presumably the sodium salt of the triazolidine-3,5-dione, formed in the sodium carbonate washings prior to acidification. In these instances the precipitate was filtered from the carbonate washings and dissolved in hot water prior to acidification. The chloroform solution was dried ($Na_2SO_4$) and evaporated under reduced pressure to give a liquid residue containing acetic anhydride. The filtered triazolidine-3,5-dione was recrystallized from 95% ethanol to yield pure 1-methylcarbonyl-4-(4-chlorophenyl)-1,2,4-triazolidine-3,5-dione as a white solid: m.p. 201°–203° C.; IR (Nujol) 1729, 1710, and 1690 cm$^{-1}$(CO); $^1$H NMR (60 MHz, $CDCl_3$ δ7.5(m, 4H), 2.5 (s, 3H). Found: C,47.31; H, 3.10; N, 16.63; M+ (70 eV) 253.0253. $C_{10}H_8N_3O_3Cl$ requires C, 47.35; H, 3.18; N, 16.57; M+ 253.0254.

General Procedure for the Synthesis of the 1,2-Dialkylcarbonyl-4-substituted-1,2,5-triazolidine-3,5-diones:

To a stirred mixture of the 4-substituted 1,2,4-triazolidine-3,5-dione (30 mmol) and lead diacetate trihydrate (60 mmol) in 200 ml of chloroform was added dropwise the carboxylic acid anhydride or appropriate acylating agent (450 mmol). The reaction mixture was stirred at room temperature until all the solids had dissolved. The solution was washed with three 100 ml portions of water and three 100 ml portions of 10% sodium carbonate. Acidification of the carbonate washings with concentrated hydrochloric acid did not produce a precipitate. The chloroform solution was dried ($Na_2SO_4$) and evaporated under reduced pressure to give a solid-liquid mixture. The mixture was filtered and the solid was recrystallized from alcohol:water to yield the pure 1,2-dialkylcarbonyl-4-substituted-1,2,4-triazolidine-3,5-dione. Acetate salts such as sodium acetate can be used in place of lead diacetate trihydrate in the reaction mixture.

Preparation of 1,2-Dimethylcarbonyl-4-phenyl-1,2,4-triazolidine-3,5-dione: To a mixture of 5.3 g (30 mmol) of 4-phenyl-1,2,4-triazolidine-3,5-dione and 22.7 g (60 mmol) of lead diacetate trihydrate in 200 ml of chloroform was added dropwise over a 15 minute period 45.9 g (450 mmol) of acetic anhydride. The mixture was stirred at room temperature. After 25 hours the pale yellow solution was washed with three 100 ml portions of water and three 75 ml portions of 10% sodium carbonate. The carbonate washings were acidified with concentrated hydrochloric acid. No precipitate was produced. The chloroform solution was dried ($Na_2SO_4$)

and evaporated under reduced pressure to give a solid-liquid residue. The residue was filtered and the filtered solid was washed with 25 ml of 95% ethanol to give 2.75 g (35.1%) of the 1,2,4-triazolidine-3,5-dione product as a white solid. An additional quantity of the product precipitated from the ethanol filtrate. This solid was filtered to give an additional 1.20 g (15.3%) of the 1,2,4-triazolidine-3,5-dione product (50.4% total yield). the solids were recrystallized from 95% ethanol to give pure 1,2-dimethylcarbonyl-4-phenyl-1,2,4-triazolidine-3,5-dione; m.p. 169°-170.5° C.; IR (Nujol) 1750, 1732 (shoulder), 1714 (shoulder) cm$^{-1}$ (CO); $^1$H NMR (60 MHz, CDCl$_3$) δ7.80(s, 5H), 2.55 (s, 6H); Found: C, 55.2; H, 4.45; N, 16.0; C$_{12}$H$_{11}$N$_3$O$_4$ requires C, 55.2; H, 4.2; N, 16.0.

Preparation of 1,2-Dimethylcarbonyl-4-(4-methoxyphenyl)-1,2,4-triazolidine-3,5-dione: To a mixture of 1.00 g (4.83 mmol) of 4-methoxyphenyl-1,2,4-triazolidine-3,5-dione and 3.80 g (10 mmol) of lead diacetate trihydrate in 40 ml of chloroform was added dropwise over a 10 minute period 7.70 g (75 mmol) of acetic anhydride. The solution was stirred at room temperature for five hours. The clear solution was washed three times with 20 ml portions of water and three times with 15 ml portions of 10% sodium carbonate. The sodium carbonate washings were acidified with concentrated hydrochloric acid. No precipitate was obtained. The chloroform solution was dried (Na$_2$SO$_4$) and evaporated to dryness under reduced pressure to give a solid-liquid residue. The residue was washed with five ml of 95% ethanol and recrystallized from methanol to give pure 1,2-dimethylcarbonyl-4-(4-chlorophenyl)-1,2,4-triazolidine-3,5-dione: m.p. 148°-150° C.; IR (Nujol) 1710, 1750 cm$^{-1}$ (CO); $^1$H NMR (300 MHz, CDCl$_3$) δ7.37-6.98 (m, 4H), 3.84 (s, 3H), 2.65(s, 6H): Found: C, 53.4; H, 4.4; N, 14.4. C$_{13}$H$_{13}$N$_3$O$_5$ requires C, 53.6; H, 4.5; N, 14.4.

Preparation of 1,2-di-n-Pentylcarbonyl-4-(4-methoxyphenyl)-1,2,4-triazolidine-3,5-dione: To a mixture of 1.00 g (4.83 mmol) of 4-methoxyphenyl-1,2,4-triazolidine-3,5-dione and 3.80 g (10 mmol) of lead diacetate trihydrate in 40 ml of chloroform was added dropwise over a 10 minute period 7.70 g (75 mmol) of hexanoic anhydride. The solution was stirred at room temperature for five hours. The clear solution was washed three times with 20 ml portions of water and three times with 15 ml portions of 10% sodium carbonate. The sodium carbonate washings were acidified with concentrated hydrochloric acid. No precipitate was obtained. The chloroform solution was dried (Na$_2$SO$_4$) and evaporated to dryness under reduced pressure to give a solid-liquid residue. The residue was washed with five ml of 95% ethanol and recrystallized from methanol to give pure 1,2-di-n-pentylcarbonyl-4-(4-methoxyphenyl)-1,2,4-triazolidine-3,5-dione: m.p. 88°-90° C.; IR (Nujol) 1742, 1710 cm$^{-1}$ (CO); $^1$H NMR (300 MHz, CDCl$_3$) δ7.36-6.97 (m, 4H), 3.83 (s, 3H), 2.97 (t, 4H), 1.76 (m, 4H), 1.35 (m, 8H), 0.89 (distorted t, 6H); Found: C, 62.3; H, 7.0; N, 10.3. C$_{21}$H$_{29}$N$_3$O$_5$ requires C, 62.5; H, 7.3; N, 10.4.

Preparation of 1,2-Diethylcarbonyl-4(4-nitrophenyl)-1,2,4-triazolidine-3,5-dione: To a mixture of 1.00 g (4.50 mmol) of 4-(4-nitrophenyl)-1,2,4-triazolidine-3,5-dione and 3.80 g (10 mmol) of lead diacetate trihydrate in 40 ml of chloroform was added dropwise over a 10 minute period 9.80 g (75 mmol) of propanoic anhydride. The solution was stirred at room temperature for five hours. The clear solution was washed three times with 20 ml portions of water and three times with 15 ml portions of 10% sodium carbonate. The sodium carbonate washings were acidified with concentrated hydrochloric acid. No precipitate was obtained. The chloroform solution was dried (Na$_2$SO$_4$) and evaporated to dryness under reduced pressure to give a solid-liquid residue. The residue was washed with five ml of 95% ethanol and recrystallized from methanol to give 1,2-diethylcarbonyl-4-(4-nitrophenyl)-1,2,4-triazolidine-3,5-dione: m.p. 140°-142° C.; IR (Nujol) 1750, 1705 cm$^{-1}$ (CO); $^1$H NMR (300 MHz, CDCl$_3$) δ8.41-7.24 (m, 4H), 3.03 (q, 4H), 1.28 (t, 6H); Found: C, 49.9; H, 4.0; N, 16.7. C$_{14}$H$_{14}$N$_4$O$_6$ requires C, 50.2; H, 4.2; N, 16.8.

Preparation of 1,2-Di-n-pentylcarbonyl-4-n-butyl-1,2,4-triazolidine-3,5-dione: To a mixture of 1.00 g (6.37 mmol) of 4-n-butyl-1,2,4-triazolidine-3,5-dione and 4.60 g (12 mmol) of lead diacetate trihydrate in 40 ml of chloroform was added dropwise over a 10 minute period 19.5 g (91 mmol) of hexanoic anhydride. The solution was stirred at room temperature for five hours. The clear solution was washed three times with 20 ml portions of water and three times with 15 ml portions of 10% sodium carbonate. The sodium carbonate washing were acidified with concentrated hydrochloric acid. No precipitate was obtained. The chloroform solution was dried (Na$_2$SO$_4$) and evaporated to dryness under reduced pressure to give a solid-liquid residue. The residue was washed with five ml of 95% ethanol and recrystallized from methanol to give pure 1,2-di-n-pentycarbonyl-4-n-butyl-1,2,4-triazolidine-3,5-dione: m.p. 88°-89° C.; IR (Nujol) 1736, 1715 cm$^{-1}$ (CO); $^1$H NMR (300 MHz, CDCl$_3$) δ2.91 (t, 4H), 1.77-1.29 (m, 18H), 0.89 (m, 9H); Found: C, 60.95; H, 8.9; N, 11.85. C$_{16}$H$_{31}$N$_3$O$_4$ requires C, 61.15; H, 8.9; N, 11.9.

Preparation of Compounds of Formula (I)(b) and (III)

Methyl diazoacetate was synthesized by the procedure of Searle, U.S. Pat. No. 2,490,714 (1949) and Chem. Abstr. 1950, 44, 3519. The 4-substituted 3-H-1,2,4-triazoline-3,5-diones were prepared by the stepwise procedure of Cookson, Gupte, Stevens, and Watts, Org. Synth., 1971, 51, 121. t-butyl hypochlorite was prepared using the method of Teeter and Bell, Org. Synth. Coll., Vol. IV, 1963, 125. Ethyl diazoacetate was purchased commercially.

Reactions of diazoalkanes with 3-H-1,2,4-triazoline-3,5(4H)-diones have been previously described. See Izydore, R.A., McLean, S., J. Am. Chem. Soc. 1975, 97, 5611.

General Procedure for the Synthesis of the 6-Alkyoxycarbonyl-3-substituted-1,3,5-triazalcyclo[3.1.0]hexane-2,4-diones;

To a solution of the 3-H-1,2,4-triazoline-3,5(4H)-dione (20 mmol) in dichloromethane (200 ml) at 0° C. was added dropwise over 10 minutes the diazolakane, with stirring. Stirring was continued until the red color of the triazolinedione had faded. The solution was then filtered and evaporated to dryness under reduced pressure. The resulting solid was purified by recrystallization by first dissolving it in hot carbon tetrachloride-chloroform (1:1), and then cooling the solution to room temperature, and finally by adding petroleum ether (b.p. 40°-60° C.) or hexane dropwise with swirling to precipitate a compound of formula (I)(b) and (III).

Preparation of 6-Ethoxycarbonyl-3-phenyl-1,3,5-triazabicyclo[3.1.0]hexane-2,4-dione: To a solution of 1.5 g (8.5 mmol) of 4-phenyl-3H-1,2,4-triazoline- 3,5(4H)-dione in 100 ml of dichloromethane at 0° C. was added dropwise over 10–20 minutes 0.97 g (8.5 mmol) of ethyl diazoacetate, with stirring. Gas evolution was noted. The deep red solution was allowed to warm to room temperature, and stirring was continued overnight. The resulting amber solution was evaporated to dryness under reduced pressure to yield 2.17 g (98%) of the crude bicyclic product. The product was purified by heating it in 20 ml of hot carbon tetrachloride, adding chloroform dropwise until the solid had dissolved, cooling the solution to room temperature, and adding petroleum ether (40°–60° C.) dropwise with swirling to precipitate pure 6-ethoxycarbonyl-3-phenyl-1,3,5-triazabicyclo[3.1.0]hexane-2,4-dione: m.p. 175°–177° C. (decomp.); IR (Nujol) 1745 cm$^{-1}$ (CO); $^1$H NMR (400 MHz, CDCl$_3$) δ1.3 (3H, br m, CH$_3$), 3.8 (1H, br s, CH), 4.3 (2H, br m, OCH$_2$), and 7.5 (5H, m, Ph); $^{13}$C NMR (100.5 MHz; CDCl$_3$; $^1$H decoupled) 13.0–14.5 (overlapping s, CH$_3$), 62.0–65.5 (overlapping s, OCH$_2$ and CH), 124.5–127.5 and 128.0–131.5 (overlapping s, Ph), and 152.8–165.0 (br overlapping s, CO). Found: C, 55.3; H, 4.1; N, 16.0; M+ (70 eV), 261. C$_{12}$H$_{11}$N$_3$O$_4$ requires C, 55.2; H, 4.25; N, 16.1; M+, 261.

Preparation of 6-Methoxycarbonyl-3-phenyl-1,3,5-triazabicyclo[3.1.0]hexane-2,4-dione: To a solution of 2.05 g (11.7 mmol) of 4-phenyl-3H-1,2,4-triazoline-3,5(4H)-dione in 100 ml of dry ethyl acetate at 0° C. under nitrogen was added dropwise over a 20 minute period 1.10 g (11 mmol) of methyl diazoacetate, with stirring. The deep red solution was kept at 0° C. for one hour and warmed to room temperature. Stirring was continued overnight. The pale yellow solution was filtered and evaporated to dryness under reduced pressure to give a light yellow solid. The solid was purified by heating it in 10 ml of hot carbon tetrachloride, adding chloroform (approximately 10 ml) to the mixture dropwise until the solid dissolved, cooling the solution to room temperature, and adding petroleum ether (b.p. 40°14 60° C.) dropwise with vigorous mixing. The precipitated solid was filtered and dried to yield 2.50 g (92%) of pure 6-methoxycarbonyl-3-phenyl-1,4,5-triazabicyclo [3.1.0]hexane-2,4-dione as a white solid: M.P. 176°–177° C. (decomp.). IR (Nujol) 1740 cm$^{-1}$ (CO); $^1$H NMR (100 MHz; CDCl$_3$ 3.75 (1H, br s, CH), 3.88 (3H, br m, OMe), and 7.45 (5H, m, Ph); $^{13}$C NMR (25.2 MHz; CDCl$_3$; $^1$H decoupled) δ54.0 (br, OMe and CH), and 123–126 and 128–131 (br, overlapping s, Ph); Found: C, 53.1; H, 3.8; N, 16.85; M+ (70 eV), 247. C$_{11}$H$_9$N$_3$O$_4$ requires, C, 53.4; H, 3.6; N, 17.0; M+, 247.

Preparation of 6-Ethoxycarbonyl-3-(4-chlorophenyl)-1,3,5-triazabicyclo[3.1.0]-hexane-2,4-dione: To a solution of 2.33 g (11 mmol) of 4-(4-chlorophenyl)-3H-1,2,4-triazoline-3,5(4H)-dione in 100 ml of dichloromethane at 0° C. under nitrogen was added dropwise over a 20 minute period 1.25 g (11 mmol) of ethyl diazaocetate. The deep red solution was kept at 0° C. for one hour and allowed to warm to room temperature. Stirring was continued overnight. The pale yellow solution was filtered and evaporated to dryness under reduced pressure to give 3.08 g (95%) of the crude bicyclic product as a light yellow solid. The solid was purified by heating it in 30 ml of hot carbon tetrachloride, adding chloroform (approximately 25 ml) dropwise until the solid dissolved, cooling the solution to room temperature, and adding petroleum ether (b.p. 40°–60° C.) dropwise with mixing. The precipitated solid was filtered and dried to yield pure 6-ethoxycarbonyl-3-(4-chlorophenyl)-1,3,5-triazabicyclo[3.1.0]hexane-2,4-dione as a white solid: M.p. 174°–176° C. (decomp.). IR (Nujol) 1740 cm$^{-1}$ (CO); $^1$H NMR (100 MHz; CDCl$_3$) δ1.3 (3H, br m, CH$_3$), 4.25(1H, br m, CH), 4.35(2H br m OCH$_2$, and 7.5 (4H, m, 4-CDClH$_4$) $^{13}$C NMR (100.5 MHz; CDCl$_3$; $^1$H decoupled) 13.0–14.5 (overlapping CH$_3$), 62.0–65.5 (overlappings, CH and OCH$_2$), and 133.2–137.5 (overlappings, 4-ClC$_6$H$_4$), and 148.0–166.0 (br overlappings, CO). Found: C, 48.6; H, 3.4; N, 14.0; M+ (70 eV), 295.0362. C$_{12}$H$_{10}$N$_3$O$_4$ requires C, 48.75; H, 3.4; N, 14.2; M+, 295.0360.

Preparation of 6-Ethoxycarbonyl-3-(4-methoxyphenyl)-1,3,5-triazabicyclo[3.1.0]-hexane-2,4-dione: To a solution of 2.28 g (11 mmol) of 4-(4-methoxyphenyl)-3H-1,2,4-triazoline-3,5(4H)-dione in 100 ml of dichloromethane at 0° C. under nitrogen was added dropwise over a 20 minute period 1.25 g (11 mmol) of ethyl diazoacetate. The deep red solution was kept at 0° C. for one hour and allowed to warm to room temperature. Stirring was continued overnight. The pale yellow solution was filtered and evaporated to dryness under reduced pressure to give 2.89 g (90%) of the crude bicyclic product as a light yellow solid. The solid was purified by heating it in 10 ml of hot carbon tetrachloride, adding chloroform (approximately 10 ml) dropwise until the solid dissolved, cooling the solution to room temperature, and adding cyclohexane dropwise with mixing. The precipitated solid was allowed to sit for two hours, filtered, washed with five ml of carbon tetrachloride, and dried to yield pure 6-ethoxycarbonyl-3-(4-methoxyphenyl)-1,3,5-triazabicyclo[3.1.0]hexane-2,4-dione as a white solid: m.p. 175°–178° C. (decomp.). IR (Nujol) 1740 cm$^{-1}$ (CO); $^1$H NMR (60 MHz; CDCl$_3$) δ1.3 (3H, br m, CH$_2$CH$_3$), 3.7 (3H, br m, OMe), 4.3 (3H, br m, CH and OCH$_2$), and 6.4–7.6 (4H, m, 4-MeO-C$_6$H$_4$). Found: C, 53.65; H, 4.7; N, 14.4. C$_{13}$H$_{13}$N$_3$O$_5$ requires C, 53.6; H, 4.5; N, 14.4.

Preparation of 6-Ethoxycarbonyl-3-n-butyl-1,3,5-triazabicyclo[3.1.0]-dione: To a solution of 1.73 g (11 mmol) of 3-n-butyl-3H-1,2,4-triazoline-3,5-(4H)-dione in 100 ml of dichloromethane at 0° C. under nitrogen was added dropwise over a 20 minute period 1.25 g (11 mmol) of ethyl diazoacetate. The deep red solution was kept at 0° C. for one hour and allowed to warm to room temperature. Stirring was continued overnight. The pale yellow solution was filtered and evaporated to dryness under reduced pressure to give 2.38 g (90%) of the crude bicyclic product as a light yellow solid. The solid was purified by dissolving it in 20 ml of carbon tetrachloride and adding cyclohexane dropwise with mixing to effect precipitation. The precipitated solid was filtered and dried to yield pure 6-ethoxycarbonyl-3-n-butyl-1,3,5-triazabicyclo[3.1.0]hexane-2,4-dione as a white solid: m.p. 94°–96° C. (decomp.); IR (Nujol) 1740 cm$^{-1}$ (CO); $^1$H NMR (60 MHz; CDCl$_3$) δ0.6–1.9 (10H, br m, CH$_3$(CH$_2$)$_2$ and CH$_3$CH$_2$O), 3.5 (2H, br m, CH$_2$N), and 4.2 (2H, br m, OCH$_2$). Found: C, 49.6; H, 6.4; N, 17.1. C$_{10}$H$_{15}$N$_3$O$_4$ requires C, 49.8; H, 6.3; N, 17.4.

Preparation of Compounds of Formula (I)(c) and (IV)

General Procedure for the Synthesis of the 6-alkoxycarbonyl-3-aryl-1,3,5-triazine-2,4(1H,3H)-diones: A solution of the bicyclic diaziridine (formula (I)(b) or (III) (20 mmol) in chlorobenzene (250 ml) was heated at reflux for two weeks. The reaction mixture was cooled to room temperature, and the precipitate was removed by filtration. The filtered solid was stirred in methylene chloride (200 ml) for 30 min and filtered to remove the triazolo[1,2-a]triazole-1,3,5,7-tetraone (25-35%). The methylene chloride solution was evaporated to dryness under reduced pressure to give the crude triazine. Purification was accomplished by recrystallization from chloroform-cyclohexane or chloroform-petroleum ether (b.p. 40°-60° C.). If necessary the recrystallized product was further purified by preparative t.l.c. on silica gel. It was necessary to heat the purified product under vacuum to drive off the purification solvents.

Preparation of 6-Ethoxycarbonyl-3-phenyl-1,3,5-triazine-2,4(1H,3H)-dione: A solution of 7.0 g (26.8 mmol) of 6-ethoxycarbonyl-3-phenyl-1,3,5-triazabicyclo[3.1.0-]hexane-2,4-dione in 250 ml of chlorobenzene was heated to reflux for two weeks during which time a precipitate slowly formed. After cooling the reaction mixture to room temperature, the precipitate was filtered to yield 3.3 g of crude solid. The solid was stirred in 200 ml of dichloromethane for 30 minutes and filtered. The filtered solid was washed with an additional 50 ml of dichloromethane to give 1.5 g (35%) of 2,6-diphenyltriazolo[1,2-a]triazole-1,3,5,7-tetraone: m.p. greater than 310° C. The combined methylene chloride washings were evaporated under reduced pressure to yield 1.5 g (21%) of crude 6-ethoxycarbonyl-3-phenyl-1,3,5-triazine-2,4(1H,3H)-dione: m.p. 158°-164° C. (decomposition). The 1,3,5-triazinedione product was purified as follows: A quantity weighing 1.00 g of the 1,3,5-triazinedione was heated in 20 ml of boiling carbon tetrachloride. To the hot mixture was added in 5 ml portions 20 ml of chloroform to dissolve the solid. The hot solution was filtered, and the filtrate was cooled to room temperature. The cool filtrate was added to 200 ml of cyclohexane at room temperature with mixing to precipitate 0.0 g of an off-white solid: m.p. 168°-170° C. In place of cyclohexane, petroleum ether (b.p. 40°-60° C.) may be substituted. It was generally observed that addition of cyclohexane to the carbon tetrachloride-chloroform filtrate led to the formation of a gummy precipitate. The off-white solid was heated at 110° C. in a heating pistol to drive off the remaining recrystallization solvents to yield pure 6-ethoxycarbonyl-3-phenyl-1,3,5-triazine-2,4(1H,3H)-dione as a white solid: M.p. 168°-170° C. (decomp.). IR (Nujol) 3440 (NH), 1746 (CO), 1779 (CO), and 1607 cm$^{-1}$ (C=N); UV$_{max}$ (MeOH) 257 nm ($\epsilon$3700); $^1$H NMR (60 MHz, acetone-d$_6$) $\delta$1.37 (3H, t, CH$_3$), 4.39 (2H, q, OCH$_2$), and 7.31 (5H, m, Ph). Found: C, 55.05; H, 4.2; N, 16.5; M+ (70 eV), 261.0747; C$_{12}$H$_{11}$N$_3$O$_4$ requires C, 55.2; H, 4.3; N, 16.1; M+, 261.0749.

Preparation of 6-ethoxycarbonyl-3-(4-chlorophenyl)-1,3,5-triazine-2,4(1H, 3H)-dione: A solution of 6.0 g (20.3 mmol) of 6-ethoxycarbonyl-3-(4-chlorophenyl)-1,3,5-triazabicyclo[3.1.0]hexane -2,4-dione in 250 ml of chlorobenzene was heated at reflux for two weeks during which time a precipitate slowly formed. After cooling the reaction mixture to room temperature, the precipitate was filtered to yield 2.13 g of crude solid. The solid was stirred in 200 ml of dichloromethane for 30 minutes and filtered. The filtered solid was washed with an additional 50 ml of dichloromethane to give 1.0 g (25% ) of 2,6-di-(4-chlorophenyl)-triazolo[1,2-a]triazol-1,3,5,7-tetraone, m.p. greater than 310° C. The combined methylene chloride washings were evaporated under reduced pressure to yield 1.08 g (18.0%) of crude 6-ethoxycarbonyl-3-(4-chlorophenyl)-1,3,5-triazine-2,4(1H,3H)-dione: m.p. 191°-196° C. (decomposition). The 1,3,5-triazinedione product was rerystallized by heating by 0.50 g of the product in 60 ml of boiling carbon tetrachloride, with stirring. A total of 55 ml of chloroform was then added in five ml portions to dissolve the solid. The hot solution was filtered, and then filtrate was cooled to room temperature. The cooled filtrate was added dropwise to 200 ml of cyclohexane with stirring to precipitate 0.21 g of an off-white solid: m.p. 203°-205° C. It was generally observed that addition of cyclohexane to the carbon tetrachloride-chloroform filtrate led to the formation of a gummy precipitate. In place of cyclohexane petroleum ether (b.p. 40°-60° C.) may be substituted. In an alternate procedure 0.80 g of the product was dissolved in 25 ml of cold acetone. The solution was filtered, and the filtrate was added slowly with swirling to precipitate 0.45 of an off-white solid: m.p. 191°-196° C. The recrystallized product was purified by preparative thin-layer chromatography (TLC) as follows: A sample of the recrystallized product weighing 0.35 g (1.2 mmol) was dissolved in 2.0 ml of HPLC grade ethyl acetate and applied in a thin streak 1.0 cm high across the bottom of 20 cm×20 cm silica TLC plates. Twelve plates were used. The plates were developed in a closed chamber using galcial acetic acid as the mobile phase. The plates were air-dried. Analysis under UV light (254 nm) revealed the presence of two components having $R_f$ values of 1.00 and 0.90, respectively. Each of the separated components was scraped from the plates and combined. Each of the components was then extracted into 50 ml of dichloromethane, filtered, and the solvent removed under reduced pressure to give a solid residue. The solid corresponding to the slower moving component ($R_f$=0.90) weighed 0.15 g: m.p. 212°-215° C. This solid was recrystallized by dissolving it in 20 ml chloroform-carbon tetrachloride (50:50) and adding the resulting solution to 100 ml of cyclohexane. The precipitate was filtered to give 0.090 g of pure 6-ethoxycarbonyl-3-(4-chlorophenyl)-1,3,5-triazine-2,4(1H,3H)-dione as a white solid: M.P. 214°-215 ° ½C. (decomp.). IR (Nujol) 3430 (NH), 1759 (CO), 1740 (CO), 1666 (CO), and 1590 cm$^{-1}$ (C=N); UV$_{max}$ (MeOH) 260 nm (3900); $^1$H NMR (60 MHz, acetone-d$_6$) $\delta$1.39 (3H, t, CH$_3$), 4.38 (2H, q, OCH$_2$), 4.8 (1H, br s, NH), and 7.37 (4H, m, 4-ClC$_6$H$_4$). Found: C, 48.65; H, 3.3; N, 14.0; M+ (70 eV), 295.0362; C$_{12}$H$_{10}$N$_3$O$_4$Cl requires C, 48.7; H, 3.4; N, 14.2; M+, 295.0360.

Pharmaceutically acceptable salts may also be prepared from other salts, including other pharmaceutically acceptable salts of the compounds of general formulas (I) through (IV), using conventional methods.

Testing of Normal Mice

The following compounds were tested for their hypolipidemic activity in CF$_1$ mice.

| Compound No. | Name |
| --- | --- |
| Parent | 1,2,4-triazolidine-3,5-dione |
| A | 4-phenyl-1-methylcarbonyl-1,2,4-triazolidine-3,5-dione |
| B | 4-phenyl-1,2-dimethylcarbonyl-1,2,4-triazolidine-3,5-dione |
| C | 4-phenyl-1-ethoxycarbonyl-1,2,4-triazolidine-3,5-dione |
| D | 4-(4-chlorophenyl)-1-methylcarbonyl-1,2,4-triazolidine-3,5-dione |
| E | 4-phenyl-1,2,4-triazolidine-3,5-dione |
| F | 4-(4-methoxyphenyl)-1,2,4-triazolidine-3,5-dione |
| G | 4-(4-n-butyl)-1,2,4-triazolidine-3,5-dione |
| H | 4-(4-nitrophenyl)-1,2,4-triazolidine-3,5-dione |
| I | 4-phenyl-1-N-phenylcarbamoyl-1,2,4-triazolidine- |

-continued

| Compound No. | Name |
|---|---|
| | 3,5-dione |
| J | 4-(4-chlorophenyl)-1,2,4-triazolidine-3,5-dione |
| K | 4-methyl-1,2,4-triazolidine-3,5-dione |
| L | 3-(4-chlorophenyl)-6-ethoxyacarbonyl-1,3,5-triazabicyclo[3.1.0]hexane-2,4-dione |
| M | 3-phenyl-6-ethoxycarbonyl-1,3,5-triazabicyclo[3.1.0]hexane-2,4-dione |
| N | 3-phenyl-6-ethoxycarbonyl-1,3,5-triazine-2,4(1H,3H)-dione |
| O | 3-(4-chlorophenyl)-6-ethoxycarbonyl-1,3,5-triazine-2,4(1H,3H)-dione |
| P | 4-(4-methoxyphenyl)-1,2-dimethylcarbonyl-1,2,4-triazolidine-3,5-dione |
| Q | 4.(4-methoxyphenyl)-1,2-diphenylcarbonyl-1,2,4-triazolidine-3,5-dione |
| R | 4.(4-methoxyphenyl)-1,2 diethylcarbonyl-1,2,4-triazolidine-3,5-dione |
| S | 4-(4-nitrophenyl)-1,2 diethylcarbonyl-1,2,4-triazolidine-3,5-dione |
| T | 4-(4-n-butyl)-1,2 dipentylcarbonyl-1,2,4-triazolidine-3,5-dione |
| U | 4-(4-chlorophenyl)-1,2-dimethylcarbonyl-1,2,4-triazolidine-3,5-dione |
| V | 4-(4-chlorophenyl)1-pentylcarbonyl (2H)-1,2,4-triazolidine-3,5 dione |

Compounds A-V as defined above, were suspended in an aqueous 1 percent carboxymethylcellulose (CMC) solution and homogenized. Each of the so prepared compounds were administered to a group of six CF$_1$ male mice, each weighing approximately 25 grams, intraperitoneally for 16 days. Each of these compounds were provided in a dosage of 20 mg/kg/d ip. On Days 9 and 16 blood was obtained by tail vein bleeding. The blood serum so obtained was separated by centrifugation for three minutes. Serum cholesterol levels were determined by a modification of the Liebermann-Burchard reaction (Ness, *Clin. Chim. Acta.*, Vol. 10, 229 [1964]). Serum triglyceride levels were determined on Day 16 by use of the Fisher, Hycel Triglyceride Test Kit.

In addition to the above-described treated mice, an untreated control group of six mice were similarly tested on Days 9 and 16 to determine their serum cholesterol and triglyceride blood levels. Based on the results obtained for the untreated control group, the percent control, based on serum cholesterol and serum triglyceride levels of the treated mice compared to the untreated mice, was obtained. Table 1 reports this percent control, including standard deviation, indicating the level of confidence of these numbers.

TABLE 1

| Compound No. | Serum Cholesterol* Day 9 | Serum Cholesterol* Day 16 | Serum Triglyceride Day 16 |
|---|---|---|---|
| Parent | 81 | 79 | 73 |
| A | 67 ± 5 | 61 ± 6 | 48 ± 6 |
| B | 70 ± 6 | 64 ± 5 | 61 ± 5 |
| C | 73 ± 7 | 69 ± 5 | 62 ± 6 |
| D | 73 ± 4 | 64 ± 6 | 55 ± 7 |
| E | 71 ± 5 | 48 ± 3 | 68 ± 6 |
| F | 75 ± 5 | 56 ± 4 | 58 ± 3 |
| G | 71 ± 6 | 69 ± 5 | 79 ± 8 |
| H | 73 ± 5 | 66 ± 5 | 47 ± 5 |
| I | 79 ± 7 | 74 ± 6 | 68 ± 6 |
| J | 90 ± 5 | 58 ± 4 | 43 ± 4 |
| K | 88 ± 6 | 67 ± 5 | 89 ± 5 |
| L | 74 ± 3 | 56 ± 5 | 66 ± 7 |
| M | 62 ± 6 | 57 ± 5 | 59 ± 6 |
| N | 63 ± 6 | 54 ± 5 | 51 ± 2 |
| O | 63 ± 4 | 57 ± 4 | 55 ± 6 |
| P | 76 | 57 | 49 |
| Q | 67 | 86 | 75 |

TABLE 1-continued

| Compound No. | Serum Cholesterol* Day 9 | Serum Cholesterol* Day 16 | Serum Triglyceride Day 16 |
|---|---|---|---|
| R | 62 | 63 | 62 |
| S | 72 | 36 | 62 |
| T | 69 | 49 | 53 |
| U | 72 | 51 | 51 |
| V | 77 | 52 | 42 |
| 1% Carbonymethyl-cellulose | 100 ± 6 | 100 ± 5 | 100 ± 7 |

*Reported as a percentage of serum cholesterol or serum triglyceride level as control + or − the standard deviation.

Testing of Hyperlipidemic Mice

A group of six CF$^1$ male mice (about 25 g) were placed on a commercial diet (U.S. Biochemical Corporation BAsal Atherogenic Test Diet) which produced a "hyperlipidemic" state. That is, the average serum cholesterol level in the group of treated mice was raised from 122 to 375 mg percent and triglyceride levels were raised from 137 to 367 mg/dL.

Upon reaching these hyperlipidemic levels, the mice were administered Compounds, A, J, M and N in a concentration of 20 mg/kg/d [LD$_{50}$ value in mice as single injection IP>500 mg/kg for these compounds] intraperitoneally for 14 days while continuing the hyperlipidemic diet. On Day 12, serum cholesterol and serum triglyceride levels were measured in accordance with the procedure of Example 6. The following results were obtained:

TABLE 2

| | Percent of Control | |
|---|---|---|
| Compound | Serum Cholesterol | Serum Triglyceride |
| A | 41 | 40 |
| J | 46 | 49 |
| M | 46 | 54 |
| N | 50 | 46 |
| Diet-Hyperlipidemic | 100 | 100 |

Serum Testing of Normal Rats

A test solution of Compounds A, F, J, M, N and O were suspended in an aqueous solution of 1% CMC, homogenized and administered orally to six Sprague-Dawley male rats, which each weighted approximately 350 grams. Administration of the compounds was by an intubation needle. The rats were each fed with 20 milligrams of Compounds A, F, J, M, N and O per kilogram of body weight per day for 14 days. Similarly, six Sprague-Dawley male rats of approximately the same weight (that used for testing F weighed approximately 160 grams) were fed similar volumes of the same aqueous 1% CMC solution without the active agents, also orally, administered by intubation needle. In addition, as a control, a similar group of six male Sprague-Dawley rats were untreated.

On Days 7 and 14, blood was obtained from each of the rats of the three groups by tail vein bleeding. The blood obtained was separated by centrifugation for three minutes. Serum cholesterol and triglyceride levels were determined in accordance with the procedure of Example 6. The following results were obtained:

TABLE 3

| | Percent of Control | | | |
|---|---|---|---|---|
| | Serum Cholesterol | | Serum Triglyceride | |
| Compound | Day 7 | Day 14 | Day 7 | Day 14 |
| A | 89 | 69 | 62 | 48 |
| F | 77 | 66 | 87 | 81 |
| J | 59 | 60 | 61 | 52 |
| M | 70 | 36 | 36 | 54 |
| N | 71 | 67 | 61 | 53 |
| O | 84 | 60 | 82 | 77 |
| 1% Carboxymethyl cellulose | 100 | 100 | 100 | 100 |

Formulations

| A. Tablet | |
|---|---|
| Ingredient | Amount per tablet |
| Active Compound | 150.0 mg |
| Lactose | 100.0 mg |
| Corn Starch | 15.0 mg |
| Magnesium stearate | 1.0 mg |

The active compound is finely ground and intimately mixed with the powdered excipients (lactose, corn starch, and magnesium stearate). The formulation is then compressed in a die to produce the tablet.

| B. Coated Tablet | |
|---|---|
| Ingredient | Amount per tablet |
| Core | |
| Active Compound | 150.0 mg |
| Corn Starch | 25.0 mg |
| Magnesium stearate | 2.0 mg |
| Coating | |
| Lactose | 200.0 mg |
| Corn Starch | 50.0 mg |
| Gelatin | 10.0 mg |

The active ingredient and starch are granulated with water and dried. Magnesium stearate is added to the dried granules. Lactose and starch are granulated with 10% w/v aqueous solution of gelatin and dried. Magnesium stearate is added to the dried coating granules. The granulated core is compressed with the granulated coating in a conventional compression molding press.

| C. Capsule | |
|---|---|
| Ingredient | Amount per Capsule |
| Active Compound | 150.0 mg |
| Lactose | 200.0 mg |
| Magnesium stearate | 10.0 mg |

The finely ground compound is mixed with the powdered excipients and packed into a two part gelatin capsule.

| D. Suspension | |
|---|---|
| Ingredient | Amount per mL |
| Active Compound | 75.0 mg |
| Sodium lauryl sulfate | 25.0 mg |
| Hydroxypropylmethylcellulose | 100.0 mg |
| Sucrose | 50.0 mg |
| Flavor and Color | q.s. |
| Water | q.s. 1.0 mL |

The sodium lauryl sulfate, hydroxypropylmethylcellulose, flavor and color are triturated with the active compound. This mixture is then blended with 0.5 ml water and sucrose, and additional water is added to make the total volume 1.0 ml of suspension.

The hypolipodemic compounds of the present invention when administered to mammals provide for a significant increase in the HDL cholesterol content (Table 4), coupled with a desirable reduction of the LDL cholesterol content. Furthermore, the very low density lipoprotein, which generally is high in triglyceride and neutral lipid content, and which carries these lipids to the tissues from the liver, is markedly reduced by the agents.

TABLE 4

The cholesterol content of serum lipoprotein of Sprague-Dawley Rats treated orally for 14 days at 20 mg/kg/day with compounds A,F,J,M,N and O is tabulated in Table 4.

| | VLDL cholesterol | Percent of Control LDL cholesterol | HDL cholesterol |
|---|---|---|---|
| Control 1% CMC compound | 100 | 100 | 100 |
| A | 44 | 74 | 441 |
| F | 59 | 78 | 141 |
| J | 98 | 43 | 194 |
| M | 71 | 67 | 340 |
| N | 50 | 87 | 409 |
| O | 27 | 78 | 113 |

We claim:

1. A pharmaceutical composition for controlling hyperlipidemia in mammals comprising of a hypolipidemically effective amount of a compound having the structure:

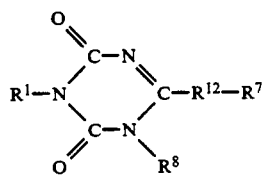

IV wherein $R^1$ is hydrogen, a $C_1$ to $C_{10}$ alkyl or substituted alkyl, a $C_2$ to $C_{10}$ alkenyl or substituted alkenyl, a $C_2$ to $C_{10}$ alkynyl or substituted alkynyl, a $C_4$ to $C_{10}$ cycloalkyl or substituted cycloalkyl, a $C_4$ to $C_{10}$ cycloalkenyl or substituted cycloalkenyl, aryl, substituted aryl, cyano, phenalkyl, —CO—$R^9$, or Y—CO—$R^9$;

$R^7$ is hydrogen, a $C_1$ to $C_{10}$ alkyl or substituted alkyl, a $C_4$ to $C_{10}$ cycloalkyl or substituted cycloalkyl, aryl or substituted aryl, aralkyl, aroxy or substituted aroxy, a $C_1$ to $C_5$ alkoxy or substituted alkoxy, —Y—CO—$R^9$, or —$NR^{10}R^{11}$;

$R^8$ is hydrogen, a $C_1$ to $C_5$ alkyl, a $C_4$ to $C_{10}$ cycloalkyl, —CO—$R^9$, or —Y—CO—$R^9$;

$R^9$ is hydrogen, a $C_1$ to $C_{10}$ alkyl or substituted alkyl, aryl or substituted aryl;

$R^{10}$ and $R^{11}$ can be the same or different and each has the same meaning as $R^9$ $R^{12}$ is —CO, —CS Y is a $C_1$ to $C_{10}$ alkylene or substituted alkylene;

with the proviso that when $R^8$ is hydrogen and $R^7$ is ethoxy, $R^1$ is not phenyl, methoxyphenyl, chlorophenyl, or n-butyl;

in combination with a pharmaceutically acceptable carrier.

2. A pharmaceutical composition for use in controlling hyperlipidemia in mammals which comprises a hypolipidemically effective amount of a compound having hypolipidemic activity and a structural formula as defined in claim 1 in combination with a pharmaceutically acceptable carrier.

3. A pharmaceutical composition for controlling hyperlipidemia in mammals which comprises a hypolipidemically effective amount of a compound having the following structural formula:

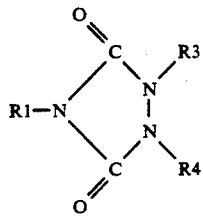
(II)

wherein $R^1$ is hydrogen, a $C_1$ to $C_5$ alkyl or substituted alkyl, a $C_2$ to $C_5$ alkenyl or substituted alkenyl, a $C_2$ to $C_5$ alkynyl or substituted alkynyl, phenyl or substituted phenyl, phenalkyl, —CO—$R^9$, or Y—CO—$R^9$;
provided that $R^1$ is not 3,5-dichlorophenyl;
$R^3$ and $R^4$ may be the same or different and are each —CO—$R^9$ or hydrogen; provided that at least one of $R^3$ and $R^4$ is —CO—$R^9$;
$R^9$ is hydrogen, a $C_1$ to $C_5$ alkyl or substituted alkyl, a $C_2$ to $C_5$ alkenyl or substituted alkenyl, a $C_2$ to $C_5$ alkynyl or substituted alkynyl;
Y is a $C_1$ to $C_5$ alkylene or substituted alkylene; and and pharmaceutically acceptable salts, and mixtures thereof;
provided that $R^1$ is not phenyl when either $R^3$ and $R^4$ is hydrogen;
and pharmaceutically acceptable salts and mixtures thereof.

4. A pharmaceutical composition for use in controlling hyperlipidemia in mammals which comprises a hypolipidemically effective amount of a compound having hypolipidemic activity and a structural formula as defined in claim 3 in combination with a pharmaceutically acceptable carrier.

5. A pharmaceutical composition for controlling hyperlipidemia in mammals comprising a hypolipidemically effective amount of a compound having the structure:

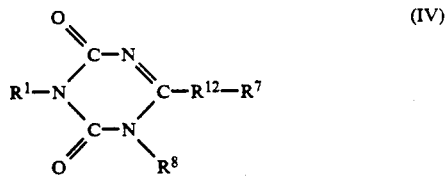
(IV)

wherein $R^1$ is is a substituted phenyl or n-butyl;
$R^7$ is hydrogen, a $C_1$ to $C_5$ alkyl or substituted alkyl, phenyl or substituted phenyl, phenalkyl, aroxy or substituted aroxy, a $C_1$ to $C_5$ alkoxy or substituted alkoxy, —Y—CO—$R^9$, or —$NR^{10}R^{11}$;
$R^8$ is hydrogen, a $C_1$ to $C_5$ alkyl;
$R^9$ is hydrogen, a $C_1$ to $C_5$ alkyl or substituted alkyl, aryl or substituted aryl;
$R^{10}$ and $R^{11}$ can be the same or different and each has the same meaning as $R^9$
$R^{12}$ is —CO, —CS
Y is a $C_1$ to $C_5$ alkylene or substituted alkylene;
and the pharmaceutically acceptable salts, and mixtures thereof;
with the proviso that when $R^8$ is hydrogen and $R^7$ is ethoxy, $R^1$ is not phenyl, methoxy phenyl, chlorophenyl, or n-butyl.

* * * * *